US009855208B2

(12) United States Patent
Wohlfart et al.

(10) Patent No.: US 9,855,208 B2
(45) Date of Patent: Jan. 2, 2018

(54) COSMETIC PRODUCTS FOR AGED SKIN

(71) Applicant: Kneipp GmbH, Würzburg (DE)

(72) Inventors: Rainer Wohlfart, Sulzfeld am Main (DE); Jürgen Blaak, Würzburg (DE); Isabel Simon, Frickenhausen am Main (DE); Peter Staib, Sulzfeld am Main (DE)

(73) Assignee: Kneipp GmbH, Würzburg (DE)

( * ) Notice: Subject to any disclaimer, the term of this patent is extended or adjusted under 35 U.S.C. 154(b) by 221 days.

(21) Appl. No.: 14/375,904

(22) PCT Filed: Mar. 15, 2013

(86) PCT No.: PCT/EP2013/055316
§ 371 (c)(1),
(2) Date: Jul. 31, 2014

(87) PCT Pub. No.: WO2013/135854
PCT Pub. Date: Sep. 19, 2013

(65) Prior Publication Data
US 2014/0370133 A1 Dec. 18, 2014

(30) Foreign Application Priority Data
Mar. 15, 2012 (EP) .................... 12159563

(51) Int. Cl.
*A61K 8/97* (2017.01)
*A61Q 19/08* (2006.01)
*A61K 36/73* (2006.01)
*A61K 8/63* (2006.01)
*A61K 8/67* (2006.01)
*A61K 8/92* (2006.01)
*A61Q 19/00* (2006.01)

(52) U.S. Cl.
CPC ................. *A61K 8/97* (2013.01); *A61K 8/63* (2013.01); *A61K 8/678* (2013.01); *A61K 8/922* (2013.01); *A61K 36/73* (2013.01); *A61Q 19/00* (2013.01); *A61Q 19/08* (2013.01); *A61K 2800/522* (2013.01); *A61K 2800/592* (2013.01)

(58) Field of Classification Search
None
See application file for complete search history.

(56) References Cited

U.S. PATENT DOCUMENTS

| 4,054,649 | A |   | 10/1977 | Cariel |
| 5,204,105 | A | * | 4/1993 | Mausner ............... A61K 8/585 424/195.16 |
| 6,395,309 | B1 |   | 5/2002 | Franz et al. |
| 6,572,862 | B1 |   | 6/2003 | Estes et al. |
| 6,572,868 | B1 |   | 6/2003 | Cope |
| 2002/0098218 | A1 | * | 7/2002 | Zhuang ............... A61K 8/63 424/401 |
| 2008/0020074 | A1 |   | 1/2008 | Courtin |

FOREIGN PATENT DOCUMENTS

| DE | 197 12 659 C1 | 8/1998 |
| DE | 10 2006 051 685 A1 | 5/2008 |
| FR | 2 294 714 A2 | 7/1976 |
| FR | 2 903 902 A1 | 1/2008 |

OTHER PUBLICATIONS

Lozano (JAOCS (1993), vol. 70, No. 6, pp. 561-565).*
Bonati (Bonati, Atillio. "Formulation of Plant Extracts Into Dosage Forms." Medicinal Plant Industry. Ed. R.O.B. Wijesekera. Boca Raton: CRC Press, 1991. Chapter 9, pp. 106-114. Print).*
PCT/EP2013/055316—International Search Report, dated Jun. 4, 2013.
PCT/EP2013/055316—International Written Opinion, dated Jun. 4, 2013.
PCT/EP2013/055316—International Preliminary Report on Patentability, dated Sep. 16, 2014.
Berardesca, "EEMCO Guidance for the Assessment of Stratum Corneum Hydration: Electrical Methods", Skin Research & Technology, May 1997, pp. 126-132, vol. 3, Issue 2, Abstract Only.
Choi, et al., "Stratum Corneum Acidification is Impaired in Moderately Aged Human and Murine Skin", Journal of Investigative Dermatology, Jun. 7, 2007, pp. 2847-2856, vol. 127, No. 12, Nature Publishing Group, GB.
Dickel, et al., "The "Strip" Patch Test: Results of a Multicentre Study towards a Standardization", Arch Dermatol Res, Oct. 2004, pp. 212-219, vol. 269, Issue 5, Abstract Only.
Gunathilake, et al., "pH-Regulated Mechanisms Account for Pigment-Type Differences in Epidermal Barrier Function", J Invest Dermatol, Jul. 2009, pp. 1719-1729, vol. 129, Issue 7.
Ivancheva, et al., "Pharmacological Activities and Biologically Active Compounds of Bulgarian Medicinal Plants", Phytochemistry: Advances in Research, Jan. 1, 2006, pp. 87-103.
Parra, et al., "EEMCO Guidance for the in Vivo Assessment of Skin Surface pH", Skin Pharmacol Appl Skin Physiol, May-Jun. 2003, pp. 188-202, vol. 16, Abstract Only.
Rogiers, "EEMCO Guidance for the Assessment of Transepidermal Water Loss in Cosmetic Sciences", Skin Pharmacol Appln Skin Physiol, Mar.-Apr. 2001, pp. 117-128, vol. 14, Issue 2, Abstract Only.
Berardesca, "EEMCO Guidance for the Assessment of Stratum Corneum Hydration: Electrical Methods", Skin Research & Technology, May 1997, pp. 126-132, vol. 3, Issue 2.
Dickel, et al., "The "Strip" Patch Test: Results of a Multicentre Study towards a Standardization", Arch Dermatol Res, Aug. 4, 2004, pp. 212-219, vol. 269, Issue 5.

(Continued)

*Primary Examiner* — Susan Hoffman
(74) *Attorney, Agent, or Firm* — Curatolo Sidoti Co., LPA; Joseph G. Curatolo; Salvatore A. Sidoti

(57) ABSTRACT

A cosmetic product having a pH value of 3.0 to 5.2 is disclosed that is specifically suitable for treating aged skin and irritations occurring there. The cosmetic product is preferably a barrier-stabilizing lotion or a barrier-stabilizing cream that contains a dry extract obtained from lady's mantle (*Alchemilla*).

13 Claims, 6 Drawing Sheets

(56) References Cited

OTHER PUBLICATIONS

J. Filipek, "The Effet of Alchemilia Xantochlora Water Extract on Lipid Peroxidation and Superoxide Anion Scavaging Activity", Pharmazie, 1992, pp. 717-718, Issue 47.

Rogiers, "EEMCO Guidance for the Assessment of Transepidermal Water Loss in Cosmetic Sciences", Skin Pharmacol Appln Skin Physiol, Mar.-Apr. 2001, pp. 117-128, vol. 14, Issue 2.

* cited by examiner

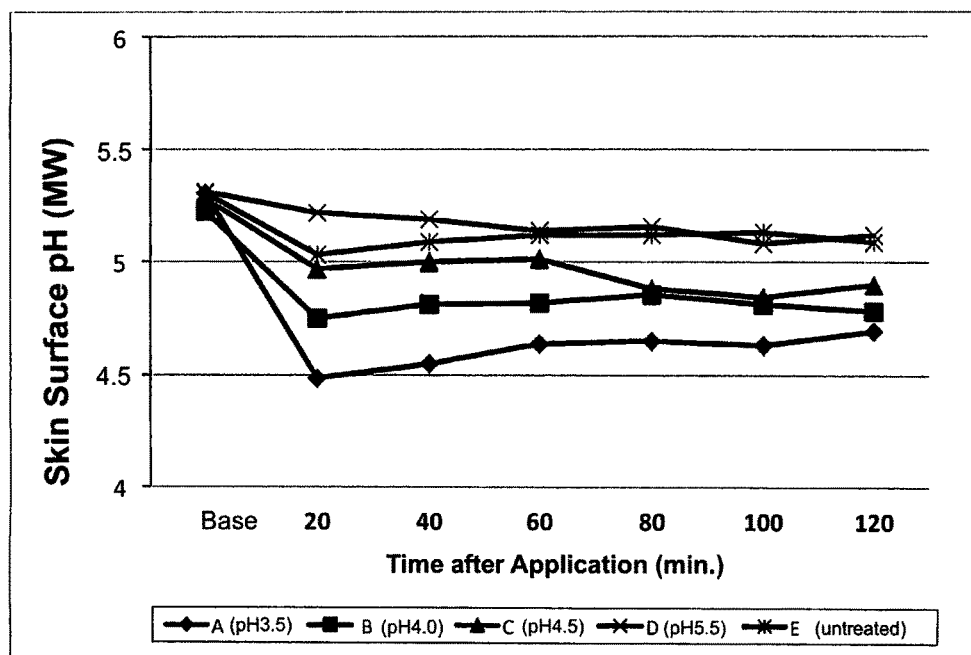
Figure 1: Presentation of the skin surface pH values (MW) of the volar forearm after application of various test products (O/W emulsions). Group of test persons: n=16 (8 male, 8 female); Age: 80-91 (MW 84 ± 3.4).

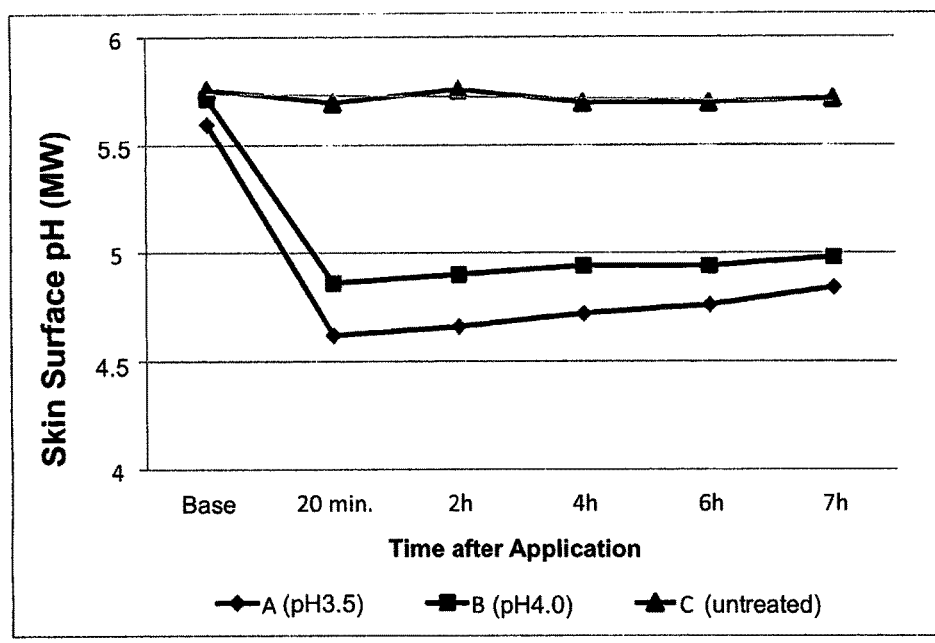
Figure 2: Presentation of the skin surface pH values (MW) of the volar forearm after application of various test products (O/W emulsions). Group of test persons: n=5 (1 male, 4 female); Age: 80-87 (MW 82.4 ± 2.7).

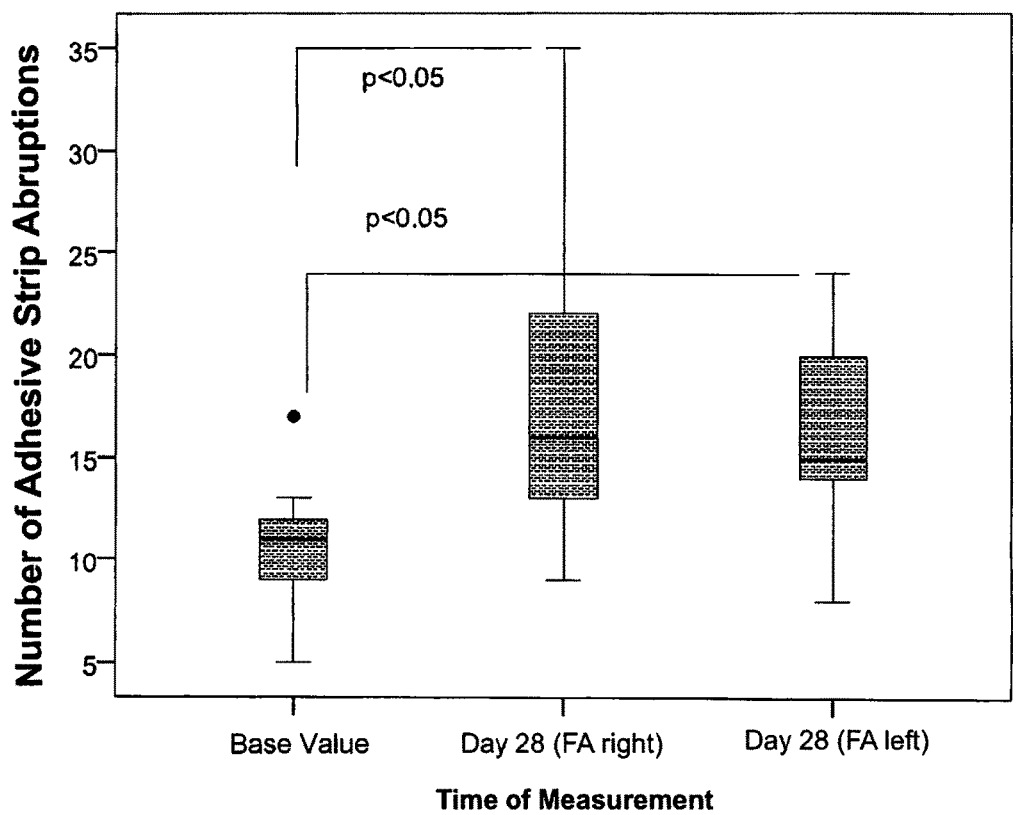
Figure 3: Presentation of the Barrier Integrity. Number of required adhesive strip abruptions until barrier damage (3-fold increase of the TEWL) before and after a four-week twice daily use of an O/W emulsion (pH 4) for whole-body care. Examination areas: Base Value (left volar forearm); Day 28 (left and right volar forearm); Group of test persons: n=13, Age: 80-90 (MW 84.5 ± 3.9); p≤ 0.05 (significant).

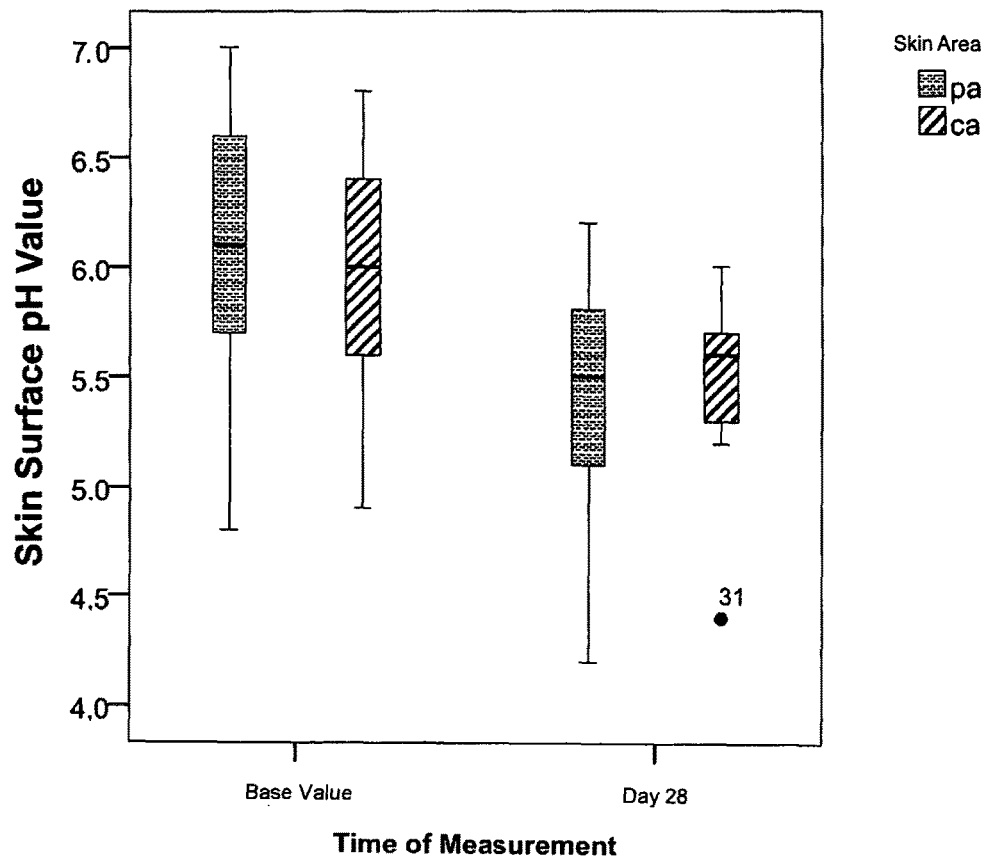
Figure 4: Change in skin surface pH value before and after a four-week twice daily use of an O/W emulsion (pH 4) for whole-body care. Examination areas: pa (forehead), ca (left upper arm); Group of test persons: n=13, Age: 80-90 (MW 84.5 ± 3.9).

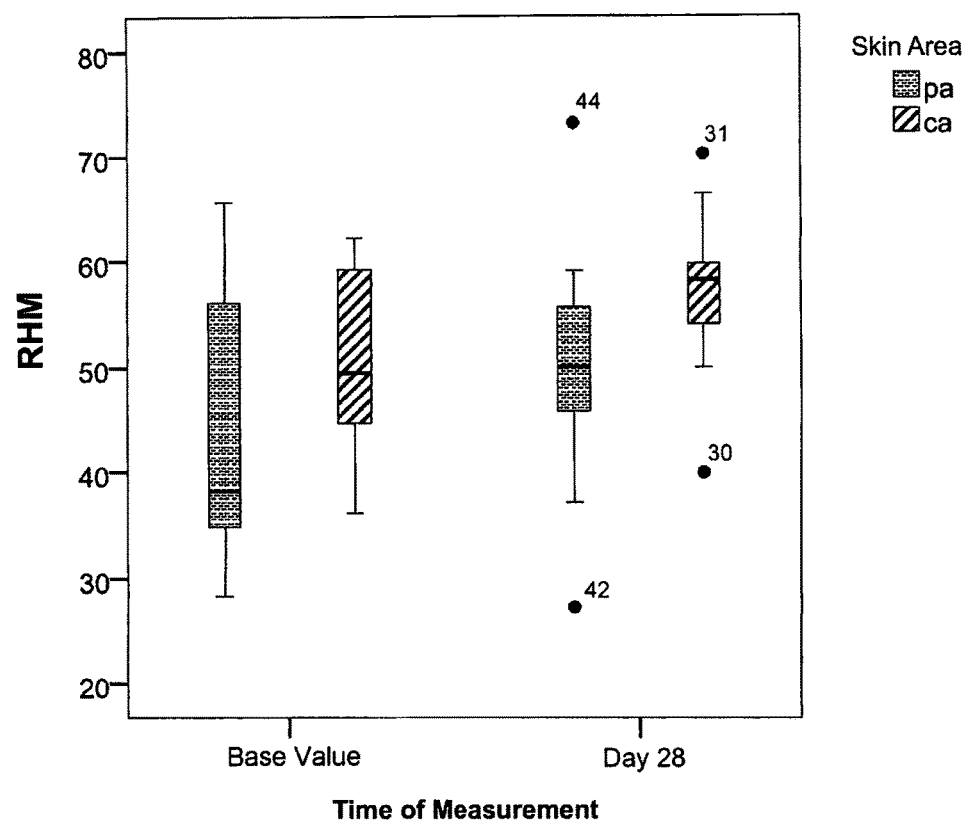
Figure 5: Change in relative horny layer moisture (RHM) before and after a four-week twice daily use of an O/W emulsion (pH 4) for whole-body care. Examination areas: pa (forehead), ca (left upper arm); Group of test persons: n=13, Age: 80-90 (MW 84.5 ± 3.9).

| Day | Parameters | | | |
|---|---|---|---|---|
| | RHM | | Skin Surface pH | |
| | ca | pa | ca | pa |
| 0 (Base Value) | 50.91 ± 9.12 | 45.00 ± 13.34 | 5.94 ± 0.58 | 6.05 ± 0.68 |
| 7 | 59.12 ± 6.96** | 54.16 ± 8.84** | 5.56 ± 0.49** | 5.49 ± 0.59** |
| 14 | 60.31 ± 10.51** | 53.12 ± 9.28* | 5.52 ± 0.76* | 5.34 ± 0.80** |
| 21 | 58.33 ± 10.37** | 52.19 ± 10.56* | 5.39 ± 0.47** | 5.28 ± 0.53*** |
| 28 | 57.45 ± 7.91* | 49.36 ± 11.27ns | 5.49 ± 0.42** | 5.44 ± 0.53*** |

Figure 6: Comparison of the relative horny layer moisture (RHM) and the skin surface pH in four-week course using an O/W emulsion (pH 4). Presentation of the mean values (± SD); ca: chronologically aged skin (left ventral upper arm); pa: light-aged skin (central forehead); ns: p > 0.05 (not significant), * p ≤ 0.05 (significant),  p ≤ 0.01 (highly significant), * p ≤ 0.001 (most significant).

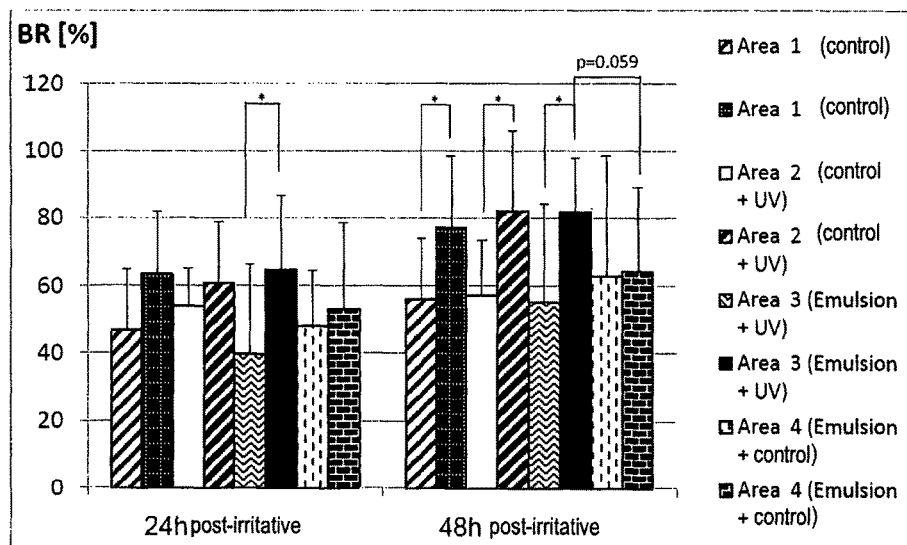

Figure 7: Percentage epidermal barrier regeneration (BR [%]) 24 and 48 hours after experimental irritation (arithmetic mean ± standard deviation). Area 1: untreated control; Area 2: UVA radiation on untreated locus (4J/cm$^2$); Area 3: pre-treated area and UVA radiation (4J/cm$^2$); Area 4: pre-treated area; Blue: Values after pre-treatment with comparative emulsion; Red: Pre-treatment with emulsion according to the invention. * = p ≤ 0.05 (significant; Wilcoxon test).

COSMETIC PRODUCTS FOR AGED SKIN

CROSS REFERENCE TO RELATED APPLICATIONS

This application is a national stage application of International Application No. PCT/EP2013/055316, filed 15 Mar. 2013, which claims priority from European Patent Application No. 12159563.1, filed 15 Mar. 2012, from which applications priority is claimed, and which are incorporated herein by reference.

The average age of the population permanently increases in the industrial nations. In particular, the number of over-60s will significantly increase in the next decades. For these sections of population products must be provided that meet the special requirements. Especially in old and in particular very old people, it is often seen that the skin is damaged or will be injured by lightest stresses. In the aged skin the physiological pH value is often increased (Choi et al. (2007): Stratum corneum acidification is impaired in moderately aged human and murine skin. *J. Invest Dermatol* 127: 2847-2856).

A variety of cosmetic compositions containing different components and additives are also known from the prior art.

FR 2903902 describes the use of a cosmetic composition for depigmenting the skin wherein an aqueous extract of lady's mantle is employed.

U.S. Pat. No. 6,572,862 B1 discloses compositions which are to protect the skin from aging. In addition to many different plant extracts also extracts of lady's mantle are mentioned.

U.S. Pat. No. 4,054,649 B1 discloses the use of *Alchemilla* in the treatment of connective tissue injuries that occur in connection with pregnancies, for example.

FR 2294714 discloses the use of an alcoholic lady's mantle extract.

DE 197 12 659 C1 claims the use of an extract of *Alchemilla vulgaris* to inhibit angiogenesis.

Object of the present invention are cosmetic products having a low pH value that positively influence epidermal structures of aged skin. Said products protect, stabilize, and enhance the function of the epidermal permeability barrier. Preferably, the cosmetic products are barrier-stabilizing emulsions.

The acid skin surface pH value has been known for a long time and according to recent studies is between 4.5 and 5. Said acid pH value of the skin surface increases from the outside to the inside and is about 7 between Stratum corneum (horny cell layer) and Stratum granulosum (granular cell layer). With this pH gradient different enzymes of different pH optimum are selectively controlled in their activity.

Enzymes with a pH optimum between 4 and 5, such as e.g. β-glucocerebrosidase and acid sphingomyelinase, are crucial for the formation of the intercellular lipid matrix of the epidermal permeability barrier that is localized in the Stratum corneum (SC).

Furthermore, serine proteases having a pH optimum of 7 are involved in the desquamation (exfoliation) of the horn cells. In case of a skin surface pH of 4.5 to 5 these enzymes are inhibited in their activity, so that no excessive desquamation and thus, imbalance between desquamation and cell renewal occurs.

Moreover, the acid skin surface pH has an antimicrobial effect. The normal flora of the skin has adapted to pH 5. By contrast, growth of pathogens, such as e.g. *staphylococcus aureus*, is inhibited at pH 5. Thus, the skin surface pH between 4.5 and 5 provides for a stabilization of the "useful" normal flora and for a defense of pathogens. Furthermore, it has been shown that an increase of the skin surface pH favors the undesired dissociation (removal) of the normal flora.

To sum it up, the skin surface pH between 4.5 and 5 is crucial for die function of the epidermal permeability barrier, because it regulates the barrier's integrity (resistance of the barrier), the barrier's cohesion (coherence of the barrier), the barrier's regeneration after damage as well as the antimicrobial defense.

(1) An increase in skin surface pH inhibits the β-glucocerebrosidase and the acid sphingomyelinase and thus, the formation of the intercellular lipid matrix, the epidermal permeability barrier.
(2) An increase in skin surface pH enhances the activity of the serine proteases, followed by an excessive desquamation and thus, reduced barrier integrity and cohesion.
(3) The increase in skin surface pH inhibits the growth of the normal flora, favors the growth of pathogens and thereby formation of dermal infections.

In inflammatory skin diseases (e.g., eczema or acne) the acid skin surface pH is increased. In the skin of neonates (<6 weeks) and the aged skin (>70 years) the skin surface pH is about 6-7.

In the 60s, skin cleansing products with a defined pH value increasingly came on the market. The background was the finding that the skin surface pH value may be strongly influenced by external agents. "pH skin neutral" products for skin cleansing were developed. These products were and are for the normal skin and are to stabilize the normal skin surface pH. Some manufacturers also recommend these products for sensitive or dry skin.

Another field on which cosmetics with a defined pH value are marketed is the area of "Chemical Peeling". By "Chemical Peeling" exfoliation of the horn cells is achieved (keratolysis) which stimulates an epidermal and dermal regeneration. "Peeling" itself is carried out with extremely acid solutions (pH value 1-2) in the doctor's office. Pre, intermediate and follow-up care of the patients is done with cosmetic products having a pH value of 3 to 4.

The cosmetic products according to the invention differ from both of the above described embodiments:

1. The cosmetic products according to the invention are not primarily intended for use with normal skin, but are a special development for specific skin conditions and inflammatory skin diseases that in particular occur with a reduced epidermal barrier function.
2. The invention must be differentiated from "Chemical Peeling", because keratolysis just should not be achieved with the invention, therefor, the products have a pH value of at least 3.0, preferably at least 3.2 and particularly preferred at least 3.5.
3. The products according to the invention are for a specific skin care for skin conditions the common feature of which is an increased skin surface pH. Moreover, the above-described skin conditions share a reduced antimicrobial barrier and thus, an enhanced susceptibility to infections.

By the application of the cosmetic products according to the invention, in particular creams, lotions, washing lotions, having a low pH value the increased skin surface pH of certain skin conditions and skin diseases can be shifted, normalized and stabilized, respectively into the normal (physiological) range between 4.5 and 5.

By normalizing the skin surface pH in particular the function of the epidermal permeability barrier (integrity, cohesion and regeneration of the barrier, relative horny layer moisture) can be improved and the function of the antimicrobial barrier can be improved.

According to the invention, generally accepted measuring methods of dermatological research were employed. The skin surface pH (Skin pH-Meter® 905; Courage & Khazaka, Cologne, Germany), the relative horny layer moisture (Corneometer® CM 825; Courage & Khazaka, Cologne, Germany) as well as the transepidermal water loss (Tewameter®™ 300; Courage & Khazaka, Cologne, Germany) were established according to the corresponding guidelines (Parra et al. (2003): EEMCO guidance for the in vivo assessment of skin surface pH. *Skin Pharmacol Appl Skin Physiol* 16: 188-202, Berardesca (1997): EEMCO guidance for the assessment of stratum corneum hydration: electrical methods. *Skin Res Technol* 3: 126-132, Rogiers (2001): EEMCO guidance for the assessment of transepidermal water loss in cosmetic sciences. *Skin Pharmacol Appl Physiol* 14: 117-128). Moreover, examination of the epidermal barrier integrity was carried out with reference to already published studies (Gunathilake et al. (2009): pH-Regulated Mechanisms Account for Pigment-Type Differences in Epidermal Barrier Function. *J Invest Dermatol* 129(7): 1719-1729).

Examination of the cosmetic products was exemplarily carried out on the skin of over 80 years old (very old) people. It has been shown in analyses of the skin of over 80 years old people that with a cosmetic product according to the invention the increased skin surface pH of the aged skin can be shifted to the physiological range between pH 4.5 and 5. After a single application the age-related increased skin surface pH was decreased within 2 (FIG. 1) and 7 hours (FIG. 2), respectively. Thus, the twice repeated daily application of the care product is sufficient to achieve a continuous normalization and stabilization of the skin surface pH, respectively. This effect was not achieved with a commercial cream of pH 5.5 (FIG. 1). Furthermore, by the four-week twice repeated daily use of a cosmetic product of pH 4 the function of the epidermal permeability barrier was improved. It has been examined, whether the four-week use of the cosmetic product of pH 4 improves the barrier integrity of the aged skin.

The barrier integrity was analyzed by taking abruptions on the forearm with an adhesive strip (3M Blenderm surgical tape; 3M Germany; Neuss; Germany). The abruption procedure is done with reference to Dickel et al. (2004): The "strip" patch test: results of a multicentre study towards a standardization. *Arch Dermatol Res* 296(5): 212-219, until the transepidermal water loss (TEWL) was increased by the 3-fold. The 3-fold increase of the TEWL is an indication for an epidermal barrier damage (Gunathilake et al. (2009): pH-Regulated Mechanisms Account for Pigment-Type Differences in Epidermal Barrier Function. *J Invest Dermatol* 129(7): 1719-1729). The less abruptions must be taken to damage the barrier (3-fold TEWL increase) the worse the barrier integrity. Before the four-week therapy (supra) an average (median value) of 11 adhesive strip abruptions were needed to damage the barrier, after the therapy 16 (right forearm) and 15 (left forearm) adhesive strip abruptions were necessary (FIG. 3), respectively. That is, that by the four-week application of a cosmetic product of pH 4 in over 80 years old people (n=13) the barrier integrity was significantly improved. Furthermore, the four-week application of the cosmetic product of pH 4 resulted in a significant decrease of the skin surface pH and a significant increase of the relative horny layer moisture (FIGS. 4-6).

By the products according to the invention the influence and stabilization of the skin surface pH of 4.5-5.0 by external supply of $H^+$ ions that are added to the products are achieved. Preferably, lowering the pH values is effected by adding physiologically harmless acids, such as lactic acid, citric acid, malic acid, tartaric acid, hydrochloric acid or phosphoric acid or their salts, such as for example disodium hydrogen phosphate or sodium dihydrogen phosphate.

In the attempts on the influence of the pH value cosmetic products were used that were identical with respect to all components and only distinguished in the pH value. Adjustment of the pH value was done with citric acid. The pH value was determined according to methods common in this field and the stability of the adjusted pH value was monitored.

Object of the present invention are cosmetic products, preferably barrier-stabilizing emulsions containing as the active ingredient an extract of lady's mantle (*Alchemilla vulgaris*) having a standardized polyphenol content, preferably in an amount of 0.025 to 3% by weight, particularly preferred 0.05 to 0.5% by weight, and especially preferred 0.075 to 0.2% by weight of the dry extract based on the finished product.

In a preferred embodiment, the cosmetic products according to the invention are barrier-stabilizing emulsions, with these in a preferred embodiment being emulsions in the form of lotions or creams.

In the context of the present invention various extracts of *Alchemilla vulgaris* prepared in a different manner have been tested with regard to phototoxicity, cytotoxicity, and antioxidative capacity. In these experiments it was found that in a particularly preferred embodiment an aqueous dry extract of *Alchemilla vulgaris* has a distinct anti-oxidative capacity.

As a measure of the anti-oxidative capacity of the dry extract that is preferably used according to the invention the so-called ORAC value (Oxygen Radical Absorbance Capacity) was examined. Here it turned out that the ORAC value of the dry extract used according to the invention preferably has at least 100000, particularly preferred at least 200000, and especially preferred at least 250000 μmol Trolox equivalents (TE)/100 g extract. The extracts used according to the invention have value of at least 250000 μmol TE/100 g, preferably at least 280000 μmol TE/100 g, measured according to the method ORAC FL. The results are given as "Trolox equivalents" (TE). In the test method the oxidative degeneration of a fluorescent molecule (for example fluorescein) is measured after mixing with a free radical-generating compound.

A further particularly preferred active component that is added to the cosmetic products according to the invention is vitamin E as well as cosmetically acceptable derivatives thereof. A particularly preferred cosmetically acceptable derivative is tocopherylacetate that is also referred to as vitamin E acetate. An advantage of the tocopherylacetate used according to the invention is that it is not oxidized in the cosmetic products and cannot penetrate the outer layers of the epidermis. According to the invention, vitamin E and tocopherylacetate, respectively, are used in an amount of 0.01-5% by weight, preferably 0.2-3.0% by weight, and particularly preferred 1.5-2.5% by weight. The weight percentages each relate to the finished product.

In a preferred embodiment, the barrier-stabilizing emulsions according to the invention have the components listed below in the respective proportions based on the finished product:

Emulsifying agents are used in an amount of 1.5 to 8, preferably 2.5 to 7 and particularly preferred 3.0 to 6.0% by weight. The emulsifying agents in part are also mixtures of the components listed below: polyoxyethylene fatty alcohol ethers, polyglycol fatty acid esters, polyoxyethylene esters with modified fatty acids; cholesterol and fatty acid esters, glyceryldilaurate, glycolstearate, disodium laurethsulfosuccinate, sodium dioctylsulfosuccinate, alcohol ethersulfate, sodium alkylarylsulfonate, polyethylene glycol alkylamines, quaternary ammonium salts, cetearylalcohol and polysorbate 20, glyceryl stearate, potassium palmitoyl; hydrolyzed wheat protein, hydrogenated lecithin, glyceryloleate.

Mixtures of various unsaturated or polyunsaturated fatty acids are used in an amount of 1.0 to 40, preferably 10 to 35, and particularly preferred 15 to 25% by weight. The fatty acids may be used in the form of fatty acids, fatty acid salts or in the form of the esters with polyhydric alcohols, such as glycerol.

As thickeners, 0.1 to 2, preferably 0.2 to 1% by weight and particularly preferred 0.25 to 0.45% by weight of the following components are used alone or in a mixture: microcrystalline cellulose, algin, xanthan gum or cosmetic acceptable acrylates, such as $C_{10}$-$C_{30}$-alkylacrylate cross-polymers.

As the humectant, in a preferred embodiment 1.0 to 20, preferably 3.0 to 10% by weight and particularly preferred 5.0 to 8.0% by weight of aqueous glycerin (85% glycerin) is added in a pharmaceutically applicable quality.

If additionally tanning agents are used these are added in an amount of 0.01 to 1, preferably 0.05 to 0.5, and particularly preferred 0.1 to 0.2% by weight. Preferred polyphenols, such as tanning agents are typical of the lady's mantle (*Alchemilla vulgaris*). Lady's mantle is characterized by a high content of polyphenols of the group of ellagitannins and gallotannins (in total between 6-8%). If the content of the individual components is given in weight percent based on drug dry extract, the lady's mantle dry extract that is preferably used according to the invention has a content of 6-8% by weight of tanning agents. Constituents of the tanning agents are gallotannins that are present in an amount of 1.0 up to 3.0% by weight, based on the drug dry extract, as well as higher amounts of ellagitannins. The ellagitannins in particular are pedunculagin that is present in an amount of 0.8 to 1.5% by weight, preferably 1.0 to 1.2% by weight, based on the drug dry extract, agrimoniin that is present in an amount between 1.0 and 4.0% by weight, preferably 2.3 to 3.6% by weight, based on the drug dry extract, as well as laevigatin that is present in an amount of 0.8 to 1.0% by weight, preferably 0.85 to 0.95% by weight.

A particularly preferred barrier-stabilizing emulsion of the present invention contains the following components in the given quantity ranges:

| Constituent | Proportion in % by weight |
| --- | --- |
| Emulsifying agent | 4 |
| Vegetable oil | 20 |
| *Alchemilla vulgaris* dry extract | 1% |
| Citric acid | for pH adjustment |
| pH value | 4.0 ± 0.2 |

The results of the examples are depicted in the figures.

BRIEF DESCRIPTION OF THE DRAWINGS

FIG. 1 represents the skin surface pH of the volar forearm after application of various test products over a period of 2 hours. These were oil-in-water emulsions only distinguishing in the pH value. Further active ingredients were not used.

FIG. 2 represents the effect of a cream with a low pH for some time after the application (up to seven hours). From FIG. 2 it can be seen that by administration of a cosmetic product according to the invention a decrease in skin surface pH below 5 can be effected for several hours.

FIG. 3 shows that after four weeks of treatment with product having a pH value of 4 the epidermal barrier integrity could be improved. The base value represents the control, that is untreated skin.

FIG. 4 shows that after four weeks of treatment with an application twice a day the skin surface pH could be decreased. The pH value was measured on predominantly light-aged (forehead, centrally) and, by way of comparison, predominantly time-aged (upper arm, ventrally) skin.

FIG. 5 shows the positive effect of a cream of pH 4 with an application twice a day over a period of four weeks regarding the increase in relative horny layer moisture. Also here, it was measured on two different places on the body (forehead, upper arm).

In FIG. 6, the relative horny layer moisture values and skin surface pH of different times of measurement are represented in a tabular form.

FIG. 7 is a graph showing the percentage of epidermal barrier regeneration 24 and 48 hours after experimental irritation on treated and untreated areas.

In the context of the present invention a significant improvement of the efficacy could be achieved by adding an extract of lady's mantle.

Thus, an object of the present invention are cosmetic products for the aged skin with a pH value of 3.0-5.2 that contain 0.1-5% by weight of an extract of lady's mantle based on the finished product.

The products according to the invention have a proportion of 0.1-5% by weight, preferably 0.2-2.5% by weight, and particularly preferred 0.2-1.0% by weight of an extract of lady's mantle, based on the finished product. This means that a cosmetic product according to the invention contains 0.1-5 g of lady's mantle extract, based on 100 g of the finished cosmetic product.

Lady's mantle belongs to the rosaceae and contains pharmacologically active ingredients, in particular tanning agents, such as gallotannins, ellagitannins (agrimoniin, laevigatin, pedunculagin), flavonoids (quercetin glycosides, leucocyanidin), phytosterols, as well as essential oils. These substances are concentrated in the dry extract used according to the invention.

In the course of the present invention it was found that a dry extract of lady's mantle extract is preferably used because it has a particularly good efficacy in view of the anti-oxidative capacity and anti-cytotoxic activity. This results in a surprisingly significant increase in the protective efficacy. An anti-oxidative action of an extract of *Alchemilla xantochlora* is described by Filipek J et al., Pharmazie 47: 717-718 (1992): The effect of *Alchemilla xantochlora* water extract on lipid peroxidation and superoxide anion scavenging activity. Pharmazie 47: 717-718).

In the course of the present invention it was surprisingly found that in cosmetic products that have been adjusted to a pH value between 3.0 and 5.2, preferably 3.2 to 4.8, a substantial barrier-stabilizing effect can be achieved by adding an aqueous extract of lady's mantle. This effect can be further improved by adding vitamin E and tocopherolacetate, respectively. However, these results also occur in normal and healthy skin, but are particularly pronounced in the aged skin and especially pronounced in the damaged aged skin. In case of damages of the aged skin, above all problems crop up such as dry skin, pruritus, contact dermatitis, eczema or fungal affect, such as candidiasis.

In a preferred embodiment, the dry extract is obtained by an aqueous extraction of the drug. Here, the plant or the pharmaceutically usable parts of the plant, respectively, are collected and dried. Then, the dried and grinded parts of the plant are extracted with water, wherein slight heating preferably to a temperature between 30 and 50° C. is supportive for the efficiency of the extraction.

The active ingredients may be prepared from the dried or also fresh plant according to various known methods. According to the invention, preferably use is made of an aqueous extract in which the mild dried parts of the plant, in particular the above-ground parts of the plant collected during the flowering period are extracted with water. For that, the parts of the plant are mild grinded, optionally under nitrogen atmosphere and extracted with water. The parts of the plant are left in water for some time (1-12 hours), with a slight heating preferably to 30° C. to at most 50° C. being preferred. Subsequently, the water is separated from the water-soluble constituents and the aqueous phase is evaporated to dryness. If it can be integrated well in the production process, the aqueous extract can also directly be worked into the cosmetic products. However, it is important that the liquid extracts are standardized in view of the dry constituents, so that the concentration of lady's mantle extract according to the invention can be maintained.

In a preferred embodiment, the cosmetic products according to the invention have a pH value between 3.2 and 4.8, with a pH value between 3.5 and 4.2 being particularly preferred.

In a further preferred embodiment, the cosmetic products according to the invention further have 0.5-2.5% by weight phytosterols, based on the total weight of the finished cosmetic product.

Preferably, the phytosterols were obtained from an oil selected from the group consisting of avocado oil, olive oil and/or rape-seed oil. The phytosterols can be worked in in a partially purified form or added in the form of the oils rich in phytosterols.

By the term phytosterols steroids with a 3-β-hydroxy group and a side chain of 8-10 C atoms on the C17 atom are understood that in particular were isolated from vegetable oil. Generally, the phytosterols are used as mixtures containing a predominant proportion of β-sitosterol, a substantial proportion of campesterol, and usually a lower proportion of sigmasterol.

According to the invention it is also possible to determine the phytosterol content of the oils used and to add a corresponding proportion of the phytosterols to the cosmetic products by specific selection of the used oils. Possibly still lacking amounts can be supplemented by adding commercially available purified phytosterol complexes, so that the concentration of 0.5-2.5% by weight, more preferably 1.0-2.0% by weight of phytosterol, based on the finished product, that is preferred according to the invention, is achieved.

In a further preferred embodiment the cosmetic products according to the invention can have a content of quercetin of 10 µg-1000 µg, preferably 50 µg-500 µg and particularly preferred 100 µg-250 µg per 100 g of the finished product.

The lady's mantle extract used according to the invention typically contains 0.6-0.7% quercetin, based on the dry extract. This content can be supplemented by adding plant extracts rich in quercetin.

Quercetin is a natural dye belonging to the flavonoids found in many plants (oak, apples, grapes and other). It is known that quercetin has an anti-cancerogen effect that can possibly be attributed to the anti-oxidative potential. Even if the mode of action of quercetin is still unknown, it is assumed that it acts as a free-radical scavenger and inactivates reactive forms of oxygen (for example superoxide anions). Reactive forms of the oxygen can also otherwise accelerate the aging process of the skin. Thus, addition of quercetin improves the protective and caring effect of the products according to the invention. The addition of quercetin is either as pure substance or preferably as enriched plant extract. Preferably used are extracts from oak bark or from the leaves of horse chestnut, apple trees or roses.

In further embodiments of the present invention also substances such as for example antiseptic substances, such as e.g. chitosan can be worked in. Also suitable are further anti-oxidative substances, such as e.g. the compounds found in mangosteen. According to the invention, such substances are added in an amount of 0.1 to 5.0% by weight, preferably 0.2 to 1.5% by weight and particularly preferred in an amount of 0.25 to 0.5% by weight, based on the finished cosmetic product.

The cosmetic products are preferably present in the form of a barrier-stabilizing emulsion, as a cream or alternatively as a lotion. The term "barrier-stabilizing emulsion" comprises both O/W lotions and O/W creams, as well as W/O lotions and W/O creams.

On the one hand, the cosmetic products according to the invention can be used to improve the condition of the aged skin. On the other hand, they are particularly suitable to treat age-related inflammatory skin conditions.

Since the cosmetic products according to the invention in the first place are skin-care products they are preferably free from surfactants that are predominantly used for cleaning.

In a preferred embodiment all constituents of the cosmetic products are of vegetable origin. Such components derived from animals, for example tallow, are not used. In this way, a potential contamination of the product with potentially pathogenic agents such as viruses or prions can be excluded.

The mechanisms of action on which the surprising synergistic efficacy of the cosmetic products according to the invention is based cannot readily be explained in a scientifically clear manner. Without wishing to be bound by any theory the present invention could be based on the basics outlined in the following:

The epidermal permeability barrier is localized in the horny layer (Stratum corneum). It is formed from protein-rich corneocytes and intercellular lipid double layers (lipid matrix). The intercellular lipids are arranged lamellar and thus, form a strongly hydrophobic, almost impermeable barrier, by which an excessive loss of water and penetration of foreign substances and microorganisms can be prevented. Consistently, the intercellular lipid matrix represents the central functional unit of the permeability barrier.

An essential aspect of the present invention is the meaning of the slightly acidic physiological skin surface pH (pH 4 to 5) for the epidermal barrier function. Formation and development of the lamellar arranged lipid matrix strongly depend on the pH as could be shown by an experimentally increased slightly acidic Stratum corneum pH (pH 4.5 to 5). By the experimental pH increase the integrity and regeneration of the epidermal barrier were significantly reduced.

The lamellar development of the lipids is induced by the activity of the two lipases "β-glucocerebrosidase" and "acid sphingomyelinase". The lipids required for the formation of the intercellular lipid matrix are synthesized in the epidermis during differentiation and released as polar lipids ("pro barrier lipids") into the transition zone between Stratum granulosum and Stratum corneum by exocytosis. Then, said polar lipids are converted to apolar barrier lipids by the pH dependent enzymes (pH optimum: 4 to 5) β-glucocerebrosidase and acid sphingomyelinase and in this way are incorporated into the intercellular lipid matrix of the Stratum corneum. This process is interfered with the age-related pH increase with the result of a reduced epidermal barrier function in later years. With the present invention the increased aged skin pH can be normalized and stabilized which in turn positively influences the activity of the mentioned lipases. So, the development of the epidermal barrier in later years is favorably influenced and can be experimentally determined as increased barrier integrity and accelerated barrier regeneration.

Since the Stratum corneum is arranged at the interface to the environment the epidermal barrier is directly and continuously exposed to environmental noxa, such as e.g. UV radiation. It is generally accepted that UV radiation (in particular UVA) results in an increased formation of "reactive oxygen species (ROS)" in the epidermis. Moreover, it has been shown that UVB and UVA radiation induce oxidation of the intercellular lipids by ROS in the Stratum corneum and reduce the function of the epidermal barrier. In addition to the oxidation of important barrier lipids and lipid fractions it has also been shown that β-glucocerebrosidase that is crucially involved in the development of the corneal lipid matrix is inhibited in its activity UV-induced.

In the aged skin, the mechanisms for the protection of the epidermal cells from oxidative stressors are reduced. An important component of the human "anti-oxidative network" to protect lipids in biomembranes is vitamin E (tocopherol). As a lipid-soluble antioxidant it prevents the lipid peroxidation of polyunsaturated fatty acids of the corneal lipid matrix by ROS. In the human Stratum corneum and in particular in the sebum high concentrations of vitamin E could be detected. Taking also into account the reduced sebaceous gland activity in later years that results in a reduction of the sebum content on the skin surface makes obvious that the vitamin E based anti-oxidative capacity in later years is reduced.

By the topical application of antioxidants the intercellular lipid matrix of the Stratum corneum is protected from lipid peroxidation and thus, from a structural change related to ROS. The α-tocopherolacetate used in the present invention builds up an "anti-oxidative protective depot" in the epidermis, because it is continuously bio-converted to the anti-oxidative acting α-tocopherol by esterases.

By way of experiments the anti-oxidative capacity of the lady's mantle extract with a high polyphenol content (ellagitannin, gallotannin, flavonoids) that was used here was shown. In contrast to the α-tocopherol that intercalates in the lipid double layers due to its lipophilic structure polyphenols (great number of hydroxyl groups) develop their anti-oxidative activity also outside of the lipid matrix, that is also in hydrophilic compartments. Moreover, polyphenols have a further anti-oxidative protection mechanism, because they are able to bind metal ions that are involved in the formation of ROS by chelation. Thus, in addition to the "reaction with peroxy radicals" by the "complexation of metal ions" a further anti-oxidative mechanism for the protection of the epidermal barrier lipids is given.

Moreover, the flavonoids are of particular interest, because they are able to strongly increase the anti-oxidative capacity of α-tocopherol in the meaning of a synergistic effect and to re-generate oxidized α-tocopherol.

By the present invention on the one hand the physiological formation of the intercellular lipid matrix in later years is normalized and favored (pH 3.0 to 5.2) and on the other hand protected by the use of two different anti-oxidatively acting components (vitamin E, lady's mantle extract). In the course of the present invention vitamin E or tocopherolacetate, respectively, and lady's mantle are preferably used in combination, because in this way surprisingly advantageous effects can be achieved. Moreover, the anti-oxidative protection of the epidermal barrier is extended to the entire Stratum corneum (including the skin surface) by the different chemical properties of the combined antioxidants (lipophilic and ambiphilic). This statement is emphasized by the described interaction between flavonoids and α-tocopherol.

Consistently, by the preferably combined topical application of vitamin E and the lady's mantle extract in an emulsion adjusted to pH 3.0 to 5.2 the epidermal permeability barrier of the aged skin is adequately formed, stabilized, and protected for a long time. The synergistic effects of the active components described herein are prerequisite for a long-term functionality of the epidermal permeability barrier in later years.

First of all, the composition of the individual cosmetic products depends on the fact whether it is a cream, an oil, a lotion or a fluid. Depending on this, the water content can vary and the composition of the individual components changes correspondingly. In a preferred embodiment, the cosmetic products according to the invention contain:

| Proportion | Preferred Ranges | Component |
| --- | --- | --- |
| 0.1-5% by weight | 0.15-1.5% by weight | lady's mantle |
| 0.1-4% by weight | 0.2-0.8% by weight | phytosterols |
| 0.1-15% by weight | 1.0-5% by weight | vegetable oils, in particular avocado oil, olive oil, almond oil and/or rape-seed oil |
| 0.01-5% by weight | 1.5-2.5% by weight | tocopherolacetate |
| 0.01-2% by weight | 0.1-0.8% by weight | thickener (for example xanthan) |
| 0.01-2% by weight | 0.2-1.0% by weight | acid regulator |
| 0.01-3.0% by weight | 0.05-1.0% by weight | citric acid (for example citric acid salts) |
| 0.01-5% by weight | 0.1-1.5% by weight | emulsifying agents |
| 0-10% by weight | 0.5-5% by weight | alcohol |
| 40-80% by weight | 50-70% by weight | purified water |

The sum of the components is always 100% by weight.

The present invention is further explained by the following examples:

EXAMPLE 1

In order to prove the synergistic effect of emulsions with a low pH value and the lady's mantle extract an experiment in healthy young test persons was carried out. For that, two emulsions were prepared. The initial emulsion had a pH value of 4.0±0.1 and contained an emulsion base, water and as comparison 4% by weight vitamin E (α-tocopherolum acetate).

The composition according to the invention was based on the same ointment base, had a pH value of 4.0±0.2 and as active ingredient 2% by weight vitamin E and 1% by weight lady's mantle dry extract.

10 test persons each applied one of the two emulsions for four weeks to the forearm. Subsequently, the test areas were exposed to UV (UVA: 4J/cm$^2$). 48 hours later, the test areas were irritated by means of adhesive strip abruptions until the TEWL (transepidermal water loss) was increased by the 3-fold. 24 and 48 hours post-irritative the TEWL was determined (measure of barrier regeneration). For comparison, 4 test areas were evaluated:

|  | left forearm | | right forearm | |
| --- | --- | --- | --- | --- |
|  | Area 1 | Area 2 | Area 3 | Area 4 |
| pre-treated |  |  | X | X |
| UVA exposed |  | X | X |  |

In the following the results are summarized.

It has been found that the barrier regeneration of the skin pre-treated with the emulsion according to the invention was significantly better, i.e. faster than that of the skin pre-treated with the comparative emulsion (only vitamin E as active ingredient). That is, the emulsion according to the invention 24 hours after exposition of the skin to UVA light results in a better barrier regeneration. Since the emulsion according to the invention does not negatively influence the skin physiological pH value of healthy young adults a significant improvement of the barrier function must be assumed especially in the older skin. With continuous use also an increase in the relative horny layer moisture is expected, so that especially in the aged skin a significant improvement of the barrier function can be expected.

EXAMPLE 2

The experimental approach shown in Example 1 was repeated. A barrier-stabilizing emulsion was prepared. Comparison was made between a barrier-stabilizing emulsion which had a pH value of 4.0±0.1 and did not contain an active ingredient and a barrier-stabilizing emulsion which in contrast to the comparative composition contained 1.0% by weight of a dry extract of lady's mantle obtained by aqueous extraction.

The experiments were carried out as described in Example 1. It was surprisingly found that the barrier-stabilizing emulsion that contained 1.0% by weight of the dry extract of lady's mantle obtained by aqueous extraction showed a much better epidermal barrier regeneration.

The results of this experiment are summarized in FIG. 7. The corresponding legend explains the experimental results.

The invention claimed is:

1. A cosmetic product having a pH value of 3.0-5.2, wherein based on the weight of the cosmetic product, the cosmetic product comprises greater than 1 to 2.5% by weight phytosterols, 0.01-5% by weight vitamin E or a derivative thereof, 0.1-5% by weight of a dry extract of lady's mantle, and a content of quercetin of 10 μg-1000 μg per 100 g of the cosmetic product.

2. The cosmetic product according to claim 1, characterized in that it has a pH value between 3.2 and 4.8.

3. The cosmetic product according to claim 1, characterized in that it has a pH value between 3.5 and 4.2.

4. The cosmetic product according to claim 1, characterized in that the dry extract is obtained by an aqueous extraction of the lady's mantle extract.

5. The cosmetic product according to claim 1, characterized in that the phytosterols are obtained from an oil selected from avocado oil, olive oil and/or rape-seed oil.

6. The cosmetic product according to claim 1, characterized in that the vitamin E derivative is tocopheryl acetate.

7. The cosmetic product according to claim 1, characterized in that it contains 2.5 to 10% by weight of an emulsifying agent based on the weight of the cosmetic product.

8. The cosmetic product according to claim 1, characterized in that it is a epidermal permeability barrier-stabilizing lotion.

9. The cosmetic product according to claim 1, characterized in that it is a epidermal permeability barrier-stabilizing cream.

10. The cosmetic product according to claim 1 for treating aged skin.

11. The cosmetic product according to claim 1 for treating age-related inflammatory skin conditions comprising eczema and/or acne.

12. A method comprising utilizing the cosmetic product according to claim 1 for improving the function of the epidermal permeability barrier.

13. The method of claim 12 wherein the cosmetic product contains 2.5 to 10% by weight of an emulsifying agent based on the weight of the cosmetic product.

* * * * *